United States Patent
Frey et al.

(10) Patent No.: US 9,655,551 B2
(45) Date of Patent: May 23, 2017

(54) DEVICE FOR PERFORMING AT LEAST ONE MEDICAL FUNCTION

(71) Applicant: Roche Diagnostics Operations, Inc., Indianapolis, IN (US)

(72) Inventors: Stephan-Michael Frey, Griesheim (DE); Helmut Walter, Heppenheim (DE); Jürgen Braun, Ehningen (DE); Jürgen Pfrang, Kallmünz (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 126 days.

(21) Appl. No.: 14/614,548

(22) Filed: Feb. 5, 2015

(65) Prior Publication Data
US 2015/0150494 A1 Jun. 4, 2015

Related U.S. Application Data

(63) Continuation of application No. 13/219,204, filed on Aug. 26, 2011, now Pat. No. 8,962,170.

(30) Foreign Application Priority Data

Aug. 27, 2010 (EP) .................................... 10174253

(51) Int. Cl.
*A61B 5/145* (2006.01)
*A61B 5/1486* (2006.01)
*A61M 5/172* (2006.01)

(52) U.S. Cl.
CPC ...... *A61B 5/14532* (2013.01); *A61B 5/14865* (2013.01); *A61M 5/1723* (2013.01); *A61B 2560/0214* (2013.01); *A61B 2560/0443* (2013.01); *Y10T 29/49108* (2015.01)

(58) Field of Classification Search
CPC .............. A61B 5/14532; A61B 5/1723; A61B 5/14865; A61B 2560/0214; A61B 2560/0443; H01M 2/10
USPC ................................ 429/100; 607/29, 34, 36
See application file for complete search history.

(56) References Cited

U.S. PATENT DOCUMENTS

| 5,149,603 A | * | 9/1992 | Fleming ............... H01M 2/1055 |
| | | | 429/100 |
| 5,938,640 A | | 8/1999 | Maget et al. |
| 6,175,752 B1 | | 1/2001 | Say et al. |
| 6,360,888 B1 | | 3/2002 | McIvor et al. |

(Continued)

FOREIGN PATENT DOCUMENTS

| CN | 101631579 A | 1/2010 |
| DE | 10341093 A1 | 4/2005 |

*Primary Examiner* — Duane Smith
(74) *Attorney, Agent, or Firm* — Harness Dickey (57) ABSTRACT

A device for performing at least one medical function on a user is proposed. The device has at least one medical functional element that is designed to perform the medical function. The medical function is selected from a diagnostic, a therapeutic and a surgical function. The device has at least one evaluation and control part that comprises at least one actuation component for controlling the medical function. The evaluation and control part has at least one casing and at least one battery receptacle. The battery receptacle comprises at least one electrical energy reservoir, more particularly at least one battery. The battery receptacle is designed to be opened irreversibly by the user for removing the energy reservoir.

20 Claims, 2 Drawing Sheets

(56) References Cited

U.S. PATENT DOCUMENTS

| | | | |
|---|---|---|---|
| 6,498,951 B1 | 12/2002 | Larson et al. | |
| 6,749,587 B2 | 6/2004 | Flaherty | |
| 8,962,170 B2 * | 2/2015 | Frey | A61B 5/14532 |
| | | | 429/100 |
| 9,065,107 B2 * | 6/2015 | Bennett | A61B 17/32002 |
| 2004/0204673 A1 | 10/2004 | Flaherty | |
| 2005/0159752 A1 | 7/2005 | Walker et al. | |
| 2008/0194961 A1 | 8/2008 | Randall | |
| 2008/0242962 A1 | 10/2008 | Roesicke et al. | |
| 2008/0284372 A1 | 11/2008 | Cover et al. | |
| 2008/0294142 A1 | 11/2008 | Patel et al. | |
| 2009/0022630 A1 | 1/2009 | Hoenes et al. | |
| 2009/0253960 A1 | 10/2009 | Takenaka et al. | |
| 2010/0130853 A1 | 5/2010 | Chandonnet et al. | |
| 2010/0191078 A1 | 7/2010 | Yodfat et al. | |
| 2010/0211011 A1 | 8/2010 | Haar | |
| 2013/0072757 A1 * | 3/2013 | Mcgrath | A61B 1/00034 |
| | | | 600/188 |

* cited by examiner

DEVICE FOR PERFORMING AT LEAST ONE MEDICAL FUNCTION

CROSS-REFERENCE TO RELATED APPLICATIONS

This application claims the benefit and priority of European Patent Application No. 10 174 253.4, filed Aug. 27, 2010. The entire disclosure of the above application is incorporated herein by reference.

BACKGROUND

The invention relates to a device for performing at least one medical function on a user. Furthermore, the invention relates to a method for disposing of components of an actuation and evaluation part of a device according to the invention, more particularly a disposable of the actuation and evaluation part. Devices according to the invention for performing at least one medical function are used, in particular, in the field of medical diagnostics or therapeutics. Thus, the device can for example be embodied as a sensor device for registering at least one bodily function of the user. By way of example, the device can be embodied as a sensor device for qualitative and/or quantitative detection of at least one analyte in a bodily fluid of the user. However, alternatively, or in addition thereto, the device can also be embodied as, for example, a medication device for administering at least one medicament to the user. A particular emphasis in the application of the present invention lies in continuous or discontinuous long-term monitoring of at least one analyte concentration in at least one bodily fluid such as, for example, interstitial fluid or blood. By way of example, glucose, cholesterol, lactate, general metabolites or other types of analytes or analyte combinations can be considered as analytes to be monitored. In principle, the present invention can also be applied to other medical fields, for example to diagnostics, therapeutics or surgery.

The prior art has disclosed a number of medical devices with diagnostic, therapeutic or surgical functions. In particular, monitoring and/or influencing certain bodily functions, more particularly monitoring one or more concentrations of specific analytes, plays a substantial role in the prevention and treatment of various diseases. Without restricting further possible applications, the invention is substantially described below with reference to blood-glucose monitoring, in particular with reference to continuous long-term blood-glucose monitoring over a number of hours, days, weeks or even months. However, in principle the invention can also be applied to other types of analyte monitoring and/or the monitoring of different types of bodily functions and to other fields in medicine. In particular, the invention can also be applied to medical therapeutics, for example to medication pumps such as insulin pumps.

Continuous measurements are also becoming ever more established in addition to so-called point measurements of one or more analytes, in which a sample of a bodily fluid is taken from a user in a targeted fashion. Thus, for example, a continuous glucose measurement in the interstitium (also referred to as continuous monitoring [CM]) has been established in the recent past as an important method for managing, monitoring and controlling a diabetes state, for example. Initially, this continuous monitoring is generally restricted to type I diabetics, i.e. diabetics who usually also wear an insulin pump. By now, use is generally made of directly implanted electrochemical sensors, which are often also referred to as needle-type sensors (NTS). Here, the active sensor region is brought directly to the measurement location, which is generally arranged in the interstitial tissue and converts glucose into electric charges, for example by using an enzyme (e.g. glucose oxidase, GOD), which charges are proportional to the glucose concentration and can be used as a measurement variable. Examples of such transcutaneous measurement systems are described in U.S. Pat. No. 6,360,888 B1 or in US 2008/0242962 A1.

Hence, current continuous monitoring systems are usually transcutaneous systems. In general, this means that the actual sensor is arranged below the skin of the user. However, an evaluation and control part of the system, which is also referred to as a patch, is generally situated outside of the body of the user, i.e. outside of the human or animal body. In the process, the sensor is generally applied by means of insertion instruments and inserted into the body tissue, which is likewise described in U.S. Pat. No. 6,360,888 B1 in an exemplary fashion. Other types of insertion instruments have also been disclosed. In general, a sensor is worn for a period of approximately one week; however, longer periods of wear, for example up to one or more months, are also possible. Thereafter, the sensitivity of the sensor generally drops off as a result of influences such as, for example, enzymes being used up and/or the sensor becoming encapsulated in the body, and hence the sensor can be expected to fail. Increasing the length of the period of wear is an area of active research. However, this means that the sensor, and optionally components such as an insertion needle directly connected thereto, should be embodied as replaceable elements. Accordingly, the sensor and, in general, further replaceable components of the device constitute a so-called disposable. However, the evaluation and control part of the system, or important, expensive parts thereof (such as e.g. high-resistance amplifier input stages and similar active elements), are generally reused, and so the device often comprises at least one reusable.

In the case of implantable sensors, the disposable generally comprises a so-called body mount, which can be affixed to the skin surface of the user, for example by means of a plaster, and by means of which the sensor that is inserted into the body tissue can be connected or is connected. The reusable, which contains the essential parts of actuation and/or evaluation electronics for measuring the analyte concentration, is then connected to this body mount. However, components can be arranged in the body mount itself. Thus, for example, at least one battery can be arranged in the body mount, and so when a body mount is replaced, and a new body mount and the reusable are assembled, the device is at the same time also equipped with a new source of energy.

The effect of this separation between disposable and reusable is that the user is not forced to replace or recharge the batteries while the sensor is used because the batteries must be replaced in any case when the body mount with the integrated battery compartment is replaced. However, according to relatively recent environmental guidelines, the batteries have to be able to be disposed of separately by the customer in the case of electrical devices that are powered by batteries. Hence, there is a challenge in developing a device that can be worn on the body of the user for a number of days in particular and hence is shielded from all acting environmental influences (damp, temperature variations, mechanical influence), wherein, however, it should at the same time be ensured that users can dispose of the batteries themselves after the period of wear.

The prior art has disclosed fundamentally different casings for medical devices, which either have completely welded-in batteries or have battery compartments that can be opened and closed a number of times. By way of example, US 2009/0253960 A1 describes an antenna unit with an antenna for receiving in-vivo information relating to a user. In the process, use is made of a cast-in antenna. In the process, flexible batteries are proposed inter alia, wherein the advantages of the flexible deformation of the cast-in battery on the body of the user are highlighted. However, separate disposal of the battery after the service life of the medical system is not possible or only possible with great difficulties.

Furthermore, the prior art has disclosed systems in which the battery can be replaced. By way of example, U.S. Pat. Nos. 6,498,951, 6,749,587 and 6,175,752 B1 illustrate various systems in which batteries can be replaced. To this end, U.S. Pat. No. 6,749,587 describes a battery compartment with a lid. U.S. Pat. Nos. 6,498,951 and 6,175,752 describe casings with two components, which can be detachably interconnected and in which provision is made for a hermetic seal of the battery compartment.

However, both known approaches have disadvantages because the above-described technical challenges are not overcome completely. Thus, in the one case, the battery cannot be disposed of separately and, in the other case, the replaceable embodiment of the battery and the technical requirements connected thereto, which relate to the battery compartment, represent significant technical challenges. In particular, in the case of battery compartments that should be opened reversibly, moisture-tightness must still be ensured because very high requirements are to be set in this respect, particularly in the case of medical devices that can be worn on the body of a user.

SUMMARY

Accordingly, it is an object of the present invention to provide a device for performing at least one medical function on a user, which device avoids the disadvantages of known devices of the aforementioned type. More particularly, firstly, a user should not be forced to replace or recharge batteries during use and, secondly, separate disposal of the batteries should be possible after use.

A device for performing at least one medical function on a user is proposed. Here, a medical function should be understood to mean a diagnostic, a therapeutic or a surgical function. A combination of various functions is also possible. In particular, the device can be embodied as a compact instrument that can be carried along by the user. More particularly, the device can be embodied as a compact instrument that can wholly or partly be worn on or in the body of the user.

The device has at least one medical functional element that is designed to perform the at least one medical function. The medical functional element is accordingly matched to the at least one medical function. By way of example, as explained above, the medical function can comprise at least one diagnostic function such that the medical functional element can for example be wholly or partly embodied as a diagnosis element, for example by it comprising at least one sensor for registering at least one bodily function. In principle, this may be any bodily functions. More particularly, the sensor can be at least one sensor for quantitative and/or qualitative detection of at least one analyte in at least one bodily fluid, for example one or more of the above-described sensors, more particularly a sensor for registering a blood-glucose concentration in a bodily fluid. By way of example, if the medical function comprises a therapeutic function, the medical functional element can for example comprise at least one therapeutic actuator that can be designed to act on at least one bodily function of the user and/or exert a stimulus on the body of the user. By way of example, this actuator can comprise at least one medication device; for example, at least one insulin pump. Alternatively, or in addition to the aforementioned medical functions and/or the aforementioned medical functional elements, the device can however also comprise other and/or further medical functions and/or medical functional elements.

In the following text, the invention is substantially described with reference to a preferred exemplary embodiment, in which the device is a device for qualitative and/or quantitative detection of an analyte in a bodily fluid, with a casing that can be applied to the skin surface of the user and a sensor that can be inserted into body tissue of the user. With the exception of the embodiment according to the invention, reference can be made to the above description of known sensors, more particularly known long-term sensors, for examples of such devices. However, in general the medical function can be selected from a diagnostic function, a therapeutic function and a surgical function, or from combinations of the aforementioned functions.

The device has at least one evaluation and control part. More particularly, this evaluation and control part can wholly or partly be embodied as a so-called patch, which is worn directly or indirectly on the skin surface of the user, for example with at least one plaster being placed therebetween. Here, within the scope of the present invention, an evaluation and control part should be understood to mean an integral component or else a component with a multi-part design that is designed to apply at least one signal, for example an electrical signal, and/or at least one form of energy, for example a current and/or a voltage, to the medical functional element and/or to prompt the medical functional element by other means to perform its medical function, and/or that is designed to record at least one electrical signal from the medical functional element, e.g. a voltage signal and/or a current signal. By way of example, recorded signals can easily be registered and/or wholly or partly converted and/or stored and/or already be evaluated or processed, at least in part. In the case of a sensor element as a medical functional element, the evaluation and actuation part can for example be designed to apply a voltage and/or a current to the sensor element, and/or it can for example comprise a measurement-value amplifier and/or a potentiostat in order to record voltage or current signals. In the case of a medication device as a medical functional element, the evaluation and actuation part can for example also comprise one or more fluidic, mechanical or fluid-mechanical components, for example a pump, a valve, a pipe system or combinations of the aforementioned and/or other elements. Various embodiments are possible.

The evaluation and actuation part can have an integral or else a multi-part design. Both options should be possible according to the invention. Without restricting other embodiments, the invention will be described below substantially with reference to multi-part embodiments of the evaluation and actuation part. Hence, the evaluation and actuation part can in particular have at least one disposable and at least one reusable. Here, a disposable is understood to mean a part of the device, more particularly of the evaluation and actuation part, that is only used once or a few times when used as intended, whereas the reusable can be used a number of times when used as intended, for example at least 5 times, at least 10 times or even at least 50 times, for example up to 500 times or more.

The disposable and the reusable can preferably be interconnected in a reversible fashion. In the case of this connection, the evaluation and actuation part, or a part thereof, can in particular be formed as a unit, which is also referred to as a patch below. The evaluation and actuation part, preferably with the disposable and the reusable, can for example be attachable to the skin surface of the user, wherein, for example, the medical functional element and/or part thereof can also project into the body tissue, for example by means of an insertion. The connection between disposable and reusable is preferably embodied in a reversible fashion. By way of example, the connection may be a force-fit and/or interlocking connection. To this end, the disposable and/or the reusable can for example each comprise one or more connection elements. By way of example, provision can be made for a plug-in connection by means of which the disposable and the reusable can be plugged together to form the unit. A unit that comprises a plurality of disposables and/or a plurality of reusables can also be implemented. The unit, made of disposable and reusable in a connected state, can more particularly have a substantially moisture-tight embodiment, for example to shield an interior of this unit from moisture.

The evaluation and actuation part, more particularly the reusable, has at least one actuation component for controlling the medical function. By way of example, the evaluation and actuation part can have at least one casing. More particularly, the reusable can have at least one reusable casing. The at least one actuation component can be arranged in the interior of the at least one casing, for example in the interior of the reusable casing. This at least one actuation component can for example comprise at least one active electronic component, for example at least one operational amplifier and/or similar electronic components. Furthermore, the actuation component can for example also comprise at least one integrated circuit. Here, an actuation component should be understood to mean a component in general, which is designed to actuate and/or register the medical function of the medical functional element, for example by applying at least one electrical current, at least one electrical voltage or another type of stimulus to the medical functional element and/or by registering at least one signal, which is generated by the medical functional element, and for example converting and/or storing it. Alternatively, or in addition thereto, the at least one actuation component can also comprise at least one mechanical, electromechanical or fluidic component for supporting and/or controlling the medical function, for example at least one pump, at least one pipe system or at least one valve. Various other embodiments are possible and, in principle, known from the prior art.

The evaluation and control part has at least one casing and at least one battery receptacle. By way of example, the disposable can have at least one disposable casing and/or the reusable can have at least one reusable casing, wherein, optionally, the disposable casing and the reusable casing can complement each other, preferably in a fluid-tight, airtight or vapor-tight fashion, to form the casing of the evaluation and control part or part of the same when the disposable is connected to the reusable. Here, within the scope of the present invention, a casing should generally be understood to mean a mechanical component that substantially determines the shape of a part completed by the casing, e.g. the evaluation and control part and/or the disposable, to the outside and protects and/or shields the part from e.g. mechanical and/or chemical influences. By way of example, the disposable casing can comprise the at least one connection element that can be used to connect the disposable to the reusable, for example one or more plug-in connectors and/or latching connectors and/or other connection elements. Alternatively, or in addition thereto, the optional disposable and the optional reusable can also be connected differently than over their casings, for example over plug-in connectors or other connectors, which are not necessarily part of the casing, or connected in another fashion. The disposable casing can in particular form a unit together with the reusable, for example by embodying the disposable casing and the reusable casing in a complementary fashion.

The battery receptacle can be embodied as a component of the casing, more particularly the disposable casing, or merely be connected to the casing, more particularly the disposable casing. Here, a battery receptacle should be understood to mean an element that is designed to hold at least one electrical energy reservoir. In the device, the battery receptacle has at least one such electrical energy reservoir. By way of example, this at least one electrical energy reservoir can comprise at least one battery. However, in principle other types of electrical energy reservoirs can also be used, independently of the term battery receptacle. By way of example, the battery receptacle can have at least one interior, for example an interior that holds the electrical energy reservoir and is hermetically sealed to the outside by the battery receptacle. By way of example, the interior can be shielded in a moisture-tight and/or airtight and/or water-vapor-tight fashion from the surroundings.

According to the invention, it is proposed that the battery receptacle is embodied such that it can be opened irreversibly by the user for removing the energy reservoir. In particular, this opening should be able to be brought about without the use of tools, for example by hand. Here, irreversible opening should be understood to mean opening during which the battery receptacle is deformed by the user such that a return to an original state is not possible, at least without using tools, aids or other auxiliary means. In particular, during the opening, a hermetically shielded interior of the battery receptacle can be irreversibly opened with respect to the surroundings such that renewed closing of the interior, during which the hermetic shield and/or seal is reinstated, cannot be achieved without aids such as e.g. adhesives, tools or the like.

In particular, the battery receptacle can comprise at least one closure element that should be opened in an irreversible fashion, more particularly a closure element that should be opened by the user, more particularly at least one sealing film, for example at least one sealing film that has been adhesively bonded and/or welded to a battery-receptacle casing of the battery receptacle. By way of example, this sealing film can hermetically seal the above-described optional interior of the battery receptacle with respect to its surroundings. By way of example, the user can open the closure element. By way of example, a manual action can open said element. Thus, the user can for example manually pull off the sealing film. Alternatively, or in addition thereto, the closure element can also be opened by automatic or semi-automatic means, for example coupled to at least one other user action. By way of example, if, as will be explained in more detail below, the casing comprises a battery-receptacle casing that can be detached from the casing, the closure element can for example be designed such that it is automatically opened when the battery-receptacle casing is detached from the casing, for example by automatically removing a sealing film. In another alternative, or in addition to the above, the closure element can for example also be opened by separating the disposable and the reusable and/or this separation may initiate the opening. By way of example, if a disposable is separated from the reusable, for example on the body surface or in a state separated from the body surface, this separation can more particularly also lead to the closure element being opened, for example to the sealing film being opened.

In particular, as described above, the battery receptacle may have at least one battery-receptacle casing. This battery-receptacle casing and the casing, more particularly the disposable casing, can be interconnected, for example by force-fit and/or interlocking connection. This connection between the battery-receptacle casing and the casing, more particularly the disposable casing, can more particularly be embodied such that it can be detached, more particularly detached in an irreversible fashion, by the user, for example under the action of customary manual forces of the user. In particular, this can be brought about by virtue of the fact that the battery-receptacle casing and/or the casing, more particularly the disposable casing, are deformed when the connection is detached, which more particularly can once again be performed manually and without the aid of tools, such that re-establishing the connection is prevented. More particularly, this can be brought about by virtue of the fact that when the battery-receptacle casing and/or the casing, more particularly the disposable casing, are separated, the battery-receptacle casing and/or the casing is kinked and/or ripped, and this prevents the connection from being re-established. More particularly, the casing, preferably the disposable casing, can have at least one predetermined breaking point, wherein the casing is deformed when the battery-receptacle casing is detached from the casing, more particularly the disposable casing, more particularly in an irreversible fashion, such that further use preferably is no longer possible. By way of example, this can be brought about by virtue of the fact that the predetermined breaking point comprises at least one weakening in the casing, more particularly in the disposable casing. More particularly, the predetermined breaking point can be embodied such that said predetermined breaking point has to be deformed, for example kinked, such that the battery-receptacle casing can be detached from the casing, more particularly the disposable casing. In general, the casing, more particularly the disposable casing, can be embodied such that the casing is broken and/or kinked during the deformation.

The casing, more particularly the disposable casing, can in particular comprise at least one base plate. Here, in general, a base plate should be understood to mean a possibly, but not necessarily, plate-shaped element that has or provides an assembly platform for the actuation and evaluation part, more particularly for the disposable. By way of example, the base plate can comprise at least one planar surface facing away from the skin surface of the user, on which surface the optional disposable can be configured and on which the optional reusable can preferably also be assembled. In particular, this base plate can have at least one receptacle region for holding the battery-receptacle casing. More particularly, this receptacle region can be arranged on a surface of the base plate facing away from the skin surface of the user. As illustrated above, the receptacle region can more particularly be embodied such that the battery-receptacle casing can only be detached from the receptacle region after the base plate has been deformed, preferably in an irreversible fashion, for example along a predetermined breaking point, more particularly a kink line. By way of example, the battery-receptacle casing can be connected to the base plate in the receptacle region by means of a force-fit and/or interlocking connection when the actuation and evaluation part, more particularly the disposable, is in the operational state. Kinking and/or another type of irreversible deformation of the base plate can, preferably in an irreversible fashion, make this force-fit and/or interlocking connection, which may comprise e.g. a latching connection, detachable. By way of example, the base plate may be able to kink along at least one kink line, wherein the battery-receptacle casing can be detached from the base plate as a result of kinking, for example by uncovering a force-fit and/or interlocking connection between the battery-receptacle casing and the base plate. Preferably there is such a deformation of the base plate that it is no longer possible to use it.

By way of example, this can in turn be brought about by using at least one predetermined breaking point, for example the aforementioned kink line.

In particular, as explained above, the battery-receptacle casing can comprise at least one closure element. By way of example, this closure element can comprise at least one sealing film. More particularly, the closure element can be embodied such that it can only be opened for the user for removing the energy reservoir from the battery receptacle once the battery-receptacle casing has been detached from the disposable casing. More particularly, the battery receptacle can be embodied to be inaccessible to the user during the operation of the device, i.e. when the battery-receptacle casing is connected to the disposable. The closure element can in particular be embodied such that it can only be opened, by the user in particular, once the battery-receptacle casing has been detached from the casing, more particularly the disposable casing. By way of example, this can be brought about by virtue of the fact that the closure element is arranged on a side of the battery-receptacle casing facing the casing, more particularly the disposable casing. Hence the closure element is only uncovered once the battery-receptacle casing is detached from the casing. In the process, the battery-receptacle casing can be detached wholly, or else partly, from the casing, more particularly the disposable casing, wherein a partial detachment can for example comprise a pivoting-open of the battery-receptacle casing, a swinging-open or the like. However, it is particularly preferred if the battery-receptacle casing can be removed completely from the casing, more particularly the disposable casing. As described above, the casing, more particularly the disposable casing, can for example have at least one base plate with at least one receptacle region for holding the battery-receptacle casing. When the battery-receptacle casing is held in the receptacle region, there can for example be an interlocking and/or force-fit connection to the base plate, which can for example be detachable by kinking and/or breaking along a predetermined breaking point, for example a kink line. The battery-receptacle casing for example can be uncovered and can be separable from the casing, more particularly the disposable casing, only after this breaking and/or kinking, such that the closure element can be opened by a user, preferably in a purely manual fashion again.

The device can be able to be affixed, more particularly wholly or partly, onto the skin surface of the user by means of an attachment element, preferably by means of at least one plaster and/or another type of self-adhesive surface. More particularly, as described above, the actuation and evaluation part, more particularly the disposable, can comprise at least one such attachment element, for example at least one such self-adhesive surface and/or at least one such plaster. By way of example, the actuation and evaluation part, more particularly the disposable, can, as described above, have at least one base plate with a support surface, which faces the skin surface of the user and can either have a self-adhesive embodiment or be fixable on the skin surface by means of at least one adhesive element. By way of example, the optional reusable can then, directly or indirectly, be placed onto or against the base plate of the casing of the actuation and evaluation part, more particularly the base plate of the disposable casing of the disposable, and can be connected to the optional disposable. Accordingly, the device can for example be embodied wholly or partly as a so-called patch, which can for example be stuck onto the skin surface. Protruding from the actuation and evaluation part, more particularly the unit made of disposable and reusable, a sensor and/or a cannula, for example, can wholly or partly extend into the body tissue of the user, i.e. through the skin of the user and into the body tissue.

In particular, the optional disposable can be embodied such that it does not comprise any electronic components itself. Here, the battery or the electrical energy reservoir and optionally present contact elements and/or conductors should not count as electrical components. In particular, passive electrical components such as e.g. electrical resistors and/or diodes and active electrical components such as e.g. operational amplifiers and/or circuits, more particularly ASICs, should count as electrical components, and these should preferably not be contained in the disposable.

As illustrated above, the functional element can perform at least one medical function. More particularly, the functional element can be selected from: a sensor for registering at least one body state of the user, more particularly a sensor for qualitative and/or quantitative registering of at least one analyte in a bodily fluid, more particularly a sensor that can be inserted into body tissue of the user; an actuator for influencing at least one body state of the user, more particularly a fluidic actuator for carrying out at least one medication function, preferably an actuator with at least one actuator part, preferably at least one cannula, that can be inserted into body tissue of the user. Various other embodiments or combinations of the aforementioned and/or other embodiments of the functional element are possible. Thus, the functional element can more particularly comprise at least one part that can be inserted into the body tissue, such as e.g. at least one sensor and/or at least one cannula.

The functional element can more particularly be connectable to the actuation and evaluation part, for example to the disposable, and/or can be part of the actuation and evaluation part, for example the disposable. The connection can have a reversible or else irreversible embodiment.

As described above, the reusable and the disposable can in a connected state form a common unit of the device. In the process, a common casing in particular can be created, which forms the casing of the actuation and evaluation part or a part thereof. This common casing can, in particular, have a substantially moisture-tight and/or vapor-tight design, more particularly in order to protect components present in the reusable and/or the disposable against moisture and/or in order to protect other components of the actuation and evaluation device and/or the electrical energy reservoir against moisture. Connection elements between the reusable and the disposable can also be shielded in a moisture-tight fashion, for example by using appropriate sealing elements such as O-rings. By way of example, this can, in a moisture-tight fashion, shield a plug-in connection between the reusable and the disposable, which connection can also comprise an electrical plug-in connection in addition to a purely mechanical plug-in function.

In addition to the above-described device in one or more of the above-described embodiments, a method is furthermore proposed for disposing of components of an actuation and evaluation part, more particularly a disposable, of a device according to the invention in one or more of the above-described embodiments. If the actuation and evaluation part contains at least one disposable and at least one reusable, then a connection between the disposable and the reusable, in particular, can be separated by this method. Furthermore, a battery receptacle is irreversibly opened in the method for removing the energy reservoir and the energy reservoir is removed from the battery receptacle. The at least one energy reservoir can subsequently be disposed of separately to the remaining components of the actuation and evaluation part, more particularly the disposable. In the method, a battery-receptacle casing of the battery receptacle in particular can be irreversibly separated from a casing of the actuation and evaluation device, more particularly a disposable casing of the disposable, more particularly by deforming at least one predetermined breaking point. The battery receptacle can subsequently be opened irreversibly to remove the energy reservoir.

The proposed device and the proposed method have a number of advantages over known devices and methods. In particular, the device can for example be embodied as a continuous monitoring sensor for glucose, which can be worn on the body of the user for a number of days, weeks or even months, during which time the glucose sensor can be implanted into the body tissue of the user. The sensor can generate an electrical current, which can be converted into a voltage that is proportional to the glucose measurement value. A wireless connection in particular can be provided for amplifying and outputting the measurement value, for example by means of at least one wireless component contained in the actuation and evaluation part, for example the reusable. The electrical energy required for this can be provided by the at least one electrical energy reservoir contained in the actuation and evaluation part, more particularly the disposable, for example over an electrical connection, more particularly an electrical plug-in connection, for example between the disposable and the reusable. For functional security and in order to maintain the quality of life of the user, the complete device can, whilst in operation, withstand all active environmental influences, such as damp, temperature variations, mechanical influences or similar influences.

The proposed option for disposal prevents the user from having to recharge the electrical energy reservoir, which would require a separate recharger. Furthermore, the long-term measurement, which typically lasts 7 days or more, does not in general have to be interrupted, for example because a rechargeable battery was not fully charged at the outset. By way of example, users themselves can undertake the above-described disposal procedure. Returning the device to the producer when the battery is empty, in exchange for a new device, is no longer necessary. This also avoids the situation where a producer or a separate disposal company receives contaminated devices, which have to be decontaminated and then laboriously refurbished.

The device can in particular be embodied as a body mount or comprise a body mount, i.e. a component that is designed to be affixed to the skin of the user. In particular, the body mount can comprise the base plate and the battery receptacle. By way of example, one or more batteries can be situated in the body mount, which batteries are housed in a battery receptacle in, for example, a disposable, which battery receptacle can be destroyed when the batteries are removed. By way of example, after a measurement, for example after 7 days of measuring, the user can open the original seal and remove the batteries and dispose of these separately. The rest of the body mount can be disposed of in domestic refuse.

Hence, the proposed device can be used to ensure that the user always has fresh batteries available for supplying the device, for example before a measurement. By way of example, this can prevent a measurement by means of the device failing because the battery voltage is too low; in the case of relatively long usage, for example 7 days of measurement or more, this constitutes a significant advantage.

The device, more particularly the common casing, which is more particularly embodied as a body mount, can in particular provide a hermetically sealed assembly. The optional disposable can form a body mount or a part thereof, which itself can be checked separately, for example independently of the reusable. In general, there is no longer a need to return contaminated assemblies to the producer. Nor is a separate charger required for the device or the electrical energy reservoir contained in this device. The user him/herself does not have to intervene in the preferably hermetically sealed system. Since the user him/herself does not insert the battery into the battery receptacle, the risk of inserting said battery with poles reversed is dispensed with. Since the user destroys the battery receptacle preferably completely and more particularly visibly during the battery removal, the reusable and more particularly the battery receptacle of the reusable can preferably never be used again. This also reduces the risk of infection.

The embodiment of the actuation and evaluation part in particular, for example the embodiment of the disposable, with at least one predetermined breaking point, for example in a base plate, more particularly a base plate of the body mount, is particularly preferred because it is particularly simple for the user to kink such a predetermined breaking point. This kink can make e.g. a battery receptacle, more particularly a battery compartment, accessible in order to dispose of batteries and/or other types of energy reservoirs. Furthermore, the actuation and evaluation part, and more particularly the disposable thereof, for example the body mount, can be changed in this manner geometrically such that further use of the body mount is rendered impossible. Thus, provision can more particularly be made for a hermetically sealed battery receptacle that is inaccessible to the user and that, at the end of its service life, can easily be broken open and/or opened irreversibly in another fashion by the user.

DRAWINGS

Further details and features of the invention emerge from the following description of preferred exemplary embodiments, which are illustrated schematically in the figures. Here, identical reference signs in the individual figures denote identical or functionally identical elements, or elements with corresponding functions. The invention is not restricted to the exemplary embodiments.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom.

Figure 1:
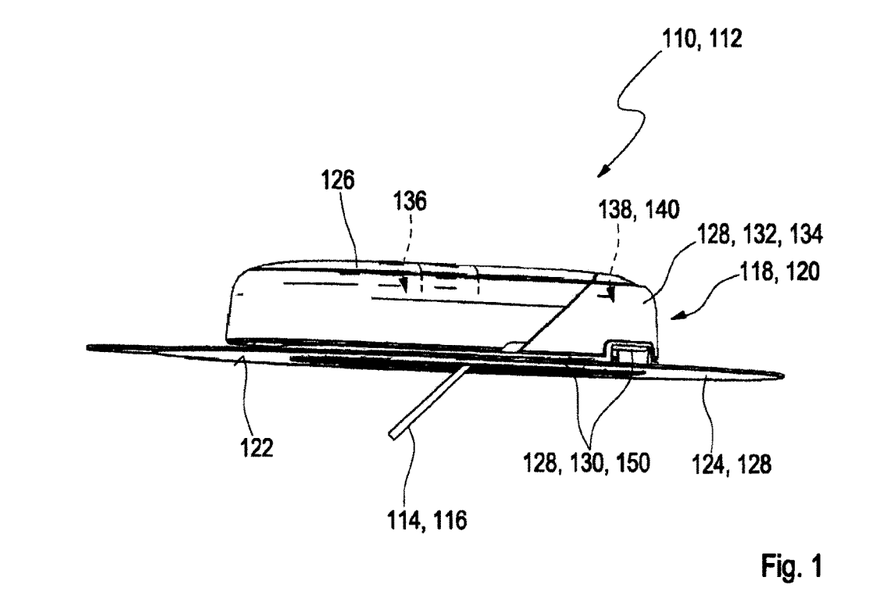
FIG. 1 shows an exemplary embodiment of a device according to the invention with a disposable and a reusable.

FIG. 1 illustrates a perspective illustration of an exemplary embodiment of a device 110 according to the invention for performing at least one medical function on a user. In the illustrated exemplary embodiment, the device 110 is embodied as a sensor device 112 for long-term monitoring of an analyte in a bodily fluid, for example for glucose monitoring, and has a medical functional element 114 in the form of a sensor 116, which can for example be embodied as an electrochemical sensor and which can be inserted into body tissue of the user through the skin surface of the user. The sensor 116 is connected to a casing 118, which can be attached to the skin surface of the user, of an evaluation and control part 120, which is also referred to as a patch. This patch 120 has a self-adhesive surface 122, which faces the skin surface, of a plaster 124.

In the illustrated exemplary embodiment, the patch 120 optionally has a multi-part design and, in the illustrated exemplary embodiment, comprises a reusable 126 and a disposable 128, of which the plaster 124 is also a part. However, this multi-part design is not mandatory, and so the illustrated example could also be modified such that the actuation and evaluation part 120 has an integral design. The disposable 128 comprises a base plate 130, which is connected to the plaster 124 and bears the reusable 126. Furthermore, a battery-receptacle casing 132 of a battery receptacle 134 is applied to the base plate 130. While the reusable 126 contains actuation and evaluation electronics 136 (not illustrated in any more detail in FIG. 1), at least one electrical energy reservoir 138 in the form of e.g. at least one battery 140 (likewise not illustrated in any more detail in FIG. 1) is held in the battery receptacle 134. The reusable 126 is reversibly connected to the disposable 128, for example over one or more connection elements 142, which can for example be identified in the separate illustration of the disposable 128 in FIG. 2A. By way of example, this can establish a hermetically sealed plug-in connection, which is embodied such that it can be detached, between the disposable 128 and the reusable 126, and so the patch 120 is created as a common unit.

As described above, a challenge in the case of devices 110 such as the device illustrated in FIG. 1 in particular consists of not having to force the user to either replace or recharge the batteries 140 while the device 110 is in use because the battery receptacle 134 is stuck onto the skin surface of the patient together with the base plate 130 during use. Secondly, despite the sealed battery receptacle 134, it should be ensured that the user can dispose of the batteries 140 separately after the period of wear.

Figure 2:
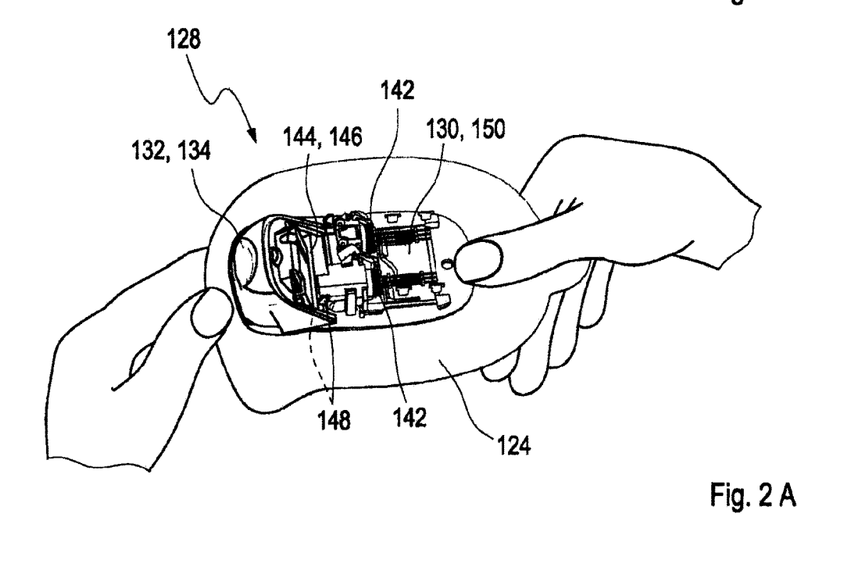
FIGS. 2A to 2C show various method steps of a method for disposing of components of the disposable of the device as per FIG. 1.
Figure 2B:
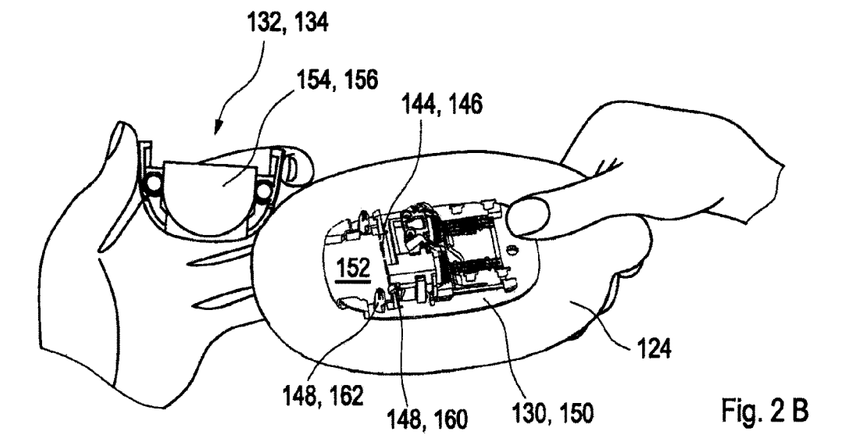
Figure 2C:
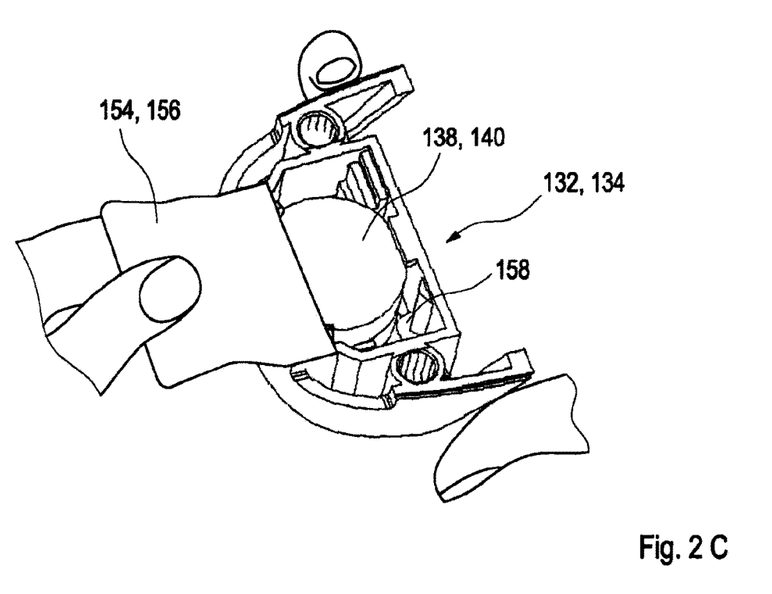

This is ensured by a special embodiment of the disposable 128, which can be identified in FIGS. 2A to 2C. FIG. 2A shows that the base plate 130 of the disposable 128 comprises a predetermined breaking point 144 in the form of a kink line 146. After the application, for example a measurement duration of 7 days, the user can pull the disposable 128, which is also referred to as a body mount, off the skin surface together with the plaster 124 and kink the base plate 130 along the predetermined breaking point 124 to the extent that the battery receptacle 134, for example a separable battery compartment, detaches from the base plate 130. Up until this point the battery receptacle 134 with its battery-receptacle casing 132 can be connected to a disposable casing 150, for example the base plate 130, by an interlocking and/or force-fit connection over e.g. one or more connection elements 148, with this connection being detached irreversibly during the kinking. As illustrated in FIG. 2B, the battery-receptacle casing 132 of the battery receptacle 134 can then be completely detached from the base plate 130 of the disposable casing 150.

The battery-receptacle casing 132 can have at least one closure element 154 on a side of the battery receptacle 134 facing a receptacle region 152 of the base plate 130 in the usage state, i.e. in the non-separated state, which closure element can preferably be opened in an irreversible fashion. In particular, this can be a sealing film 156 adhesively bonded and/or welded to the battery-receptacle casing 132, which film can have a transparent or else opaque embodiment and can be produced, for example, from a plastic material and/or a metallic material and/or a laminate material. By pulling off this sealing film 156, as illustrated in FIG. 2C, the battery 140 can be removed from the battery receptacle 134 or the interior 158 thereof, which preferably was previously hermetically sealed by the sealing film 156. This allows a separate disposal of the batteries 140, which is independent of the disposal of the remainder of the disposable 128.

FIGS. 2B and 2C once again allow identification of details of the connection elements 148. Thus, it is possible to identify that these connection elements can firstly comprise a latching connection 160 and secondly for example also a plug-in connection 162 in addition thereto or as an alternative thereto. However, in principle, other embodiments are also possible. By kinking the predetermined breaking point 144 along the kink line 146, the base plate 130 loses its rigid shape such that the latching connection 160 would not re-latch even if the plug-in connection 162 were re-established, and so the separation of the battery receptacle 134 from the base plate 130 is irreversible.

LIST OF REFERENCE NUMERALS

110 Device for performing at least one medical function
112 Sensor device
114 Medical functional element
116 Sensor
118 Casing
120 Evaluation and control part (patch)
122 Self-adhesive surface
124 Plaster
126 Reusable
128 Disposable
130 Base plate
132 Battery-receptacle casing
134 Battery receptacle
136 Actuation and evaluation electronics
138 Electrical energy reservoir
140 Battery
142 Connection elements
144 Predetermined breaking point
146 Kink line
148 Connection element
150 Disposable casing
152 Receptacle region
154 Closure element
156 Sealing film
158 Interior
160 Latching connection
162 Plug-in connection

What is claimed is:

1. A medical device comprising a casing having a battery receptacle connected thereto, the casing comprising a sensor or a cannula connected thereto and configured to contact a bodily fluid sample within a patient's body, the battery receptacle housing a battery therein and having a closure element that is only movable once from a closed and sealed condition to an open condition and is subsequently immovable from the open condition to the closed and sealed condition, the battery being removable from the battery receptacle only when the closure element is in the open condition,
wherein the closure element includes a sealing film attached to the battery-receptacle casing by adhesive bonding or by welding or by adhesively bonding and welding.

2. The medical device of claim 1, wherein the battery receptacle is detachable from the casing.

3. The medical device of claim 2, wherein the casing comprises a sensor and houses an evaluation circuit that processes a signal from the sensor indicative of the bodily fluid, and wherein the battery is disconnected from the evaluation circuit when the battery receptacle is detached from the casing.

4. The medical device of claim 2, wherein a battery receptacle casing of the battery receptacle is deformed when the battery receptacle is detached from the casing.

5. The medical device of claim 2, wherein the casing is deformed when the battery receptacle is detached from the casing.

6. The medical device of claim 1, wherein the battery receptacle is detachable from the casing at a predetermined breaking point.

7. The medical device of claim 6, wherein the predetermined breaking point includes a kink line.

8. The medical device of claim 1, wherein the battery receptacle is irreversibly detachable from the casing.

9. The medical device of claim 1, wherein the casing includes an adhesive surface configured to adhere the medical device to the patient's skin.

10. The medical device of claim 1, wherein the casing comprises a sensor and a cannula.

11. A medical device comprising a casing having a battery receptacle connected thereto, the casing having a sensor and/or a cannula connected thereto and configured to contact a bodily fluid sample within a patient's body, the battery receptacle receiving a battery and being irreversibly detachable from the casing such that detachment of the battery receptacle from the casing prevents the battery receptacle from being subsequently reattached to the casing,
wherein a battery receptacle casing of the battery receptacle is deformed when the battery receptacle is detached from the casing.

12. The medical device of claim 11, wherein the casing comprises a sensor and houses an evaluation circuit that processes a signal from the sensor indicative of the bodily fluid, and wherein the battery is disconnected from the evaluation circuit when the battery receptacle is detached from the casing.

13. The medical device of claim 12, wherein the battery receptacle includes a closure element that is only movable once from a closed and sealed condition to an open condition and is subsequently immovable from the open condition to the closed and sealed condition, and wherein the battery is removable from the battery receptacle only when the closure element is in the open condition.

14. The medical device of claim 13, wherein the closure element includes a sealing film attached to the battery-receptacle casing by adhesive bonding or by welding or by adhesively bonding and welding.

15. A medical device comprising a casing having a battery receptacle connected thereto, the casing having a sensor and/or a cannula connected thereto and configured to contact a bodily fluid sample within a patient's body, the battery receptacle receiving a battery and being irreversibly detachable from the casing such that detachment of the battery receptacle from the casing prevents the battery receptacle from being subsequently reattached to the casing,
 wherein the casing is deformed when the battery receptacle is detached from the casing.

16. The medical device of claim 11, wherein the battery receptacle is detachable from the casing at a predetermined breaking point.

17. A medical device comprising a casing having a battery receptacle connected thereto, the casing having a sensor and/or a cannula connected thereto and configured to contact a bodily fluid sample within a patient's body, the battery receptacle receiving a battery and being irreversibly detachable from the casing such that detachment of the battery receptacle from the casing prevents the battery receptacle from being subsequently reattached to the casing,
 wherein the battery receptacle is detachable from the casing at a predetermined breaking point,
 wherein the predetermined breaking point includes a kink line.

18. The medical device of claim 11, wherein the casing includes an adhesive surface configured to adhere the medical device to the patient's skin.

19. The medical device of claim 15, wherein the battery receptacle includes a closure element that is only movable once from a closed and sealed condition to an open condition and is subsequently immovable from the open condition to the closed and sealed condition, and wherein the battery is removable from the battery receptacle only when the closure element is in the open condition.

20. The medical device of claim 17, wherein the battery receptacle includes a closure element that is only movable once from a closed and sealed condition to an open condition and is subsequently immovable from the open condition to the closed and sealed condition, and wherein the battery is removable from the battery receptacle only when the closure element is in the open condition.

\* \* \* \* \*